US008622932B2

(12) United States Patent
Matsumoto et al.

(10) Patent No.: US 8,622,932 B2
(45) Date of Patent: Jan. 7, 2014

(54) GUIDEWIRE

(75) Inventors: Satoru Matsumoto, Aichi (JP); Masayuki Takahashi, Aichi (JP)

(73) Assignee: Asahi Intecc Co., Ltd., Aichi (JP)

( * ) Notice: Subject to any disclaimer, the term of this patent is extended or adjusted under 35 U.S.C. 154(b) by 374 days.

(21) Appl. No.: 12/973,252

(22) Filed: Dec. 20, 2010

(65) Prior Publication Data

US 2011/0160705 A1 Jun. 30, 2011

(30) Foreign Application Priority Data

Dec. 25, 2009 (JP) ................................ 2009-293660
Apr. 15, 2010 (JP) ................................ 2010-093858
Apr. 16, 2010 (JP) ................................ 2010-094730

(51) Int. Cl.
*A61B 5/00* (2006.01)

(52) U.S. Cl.
USPC ........................................................ 600/585

(58) Field of Classification Search
USPC ........................................................ 600/585
See application file for complete search history.

(56) References Cited

U.S. PATENT DOCUMENTS

| 5,063,935 | A | 11/1991 | Gambale |
| 5,345,945 | A | 9/1994 | Hodgson et al. |
| 5,678,296 | A | 10/1997 | Fleischhacker et al. |
| 5,957,903 | A | 9/1999 | Mirzaee et al. |
| 6,679,853 | B1 * | 1/2004 | Jalisi ........................ 600/585 |
| 7,077,811 | B2 | 7/2006 | Vrba et al. |
| 7,399,283 | B2 | 7/2008 | Kato |
| 2004/0167442 | A1 | 8/2004 | Shireman et al. |
| 2005/0054950 | A1 | 3/2005 | Parins |
| 2006/0235337 | A1 | 10/2006 | Vrba et al. |
| 2008/0214959 | A1 | 9/2008 | Miyata et al. |
| 2009/0005706 | A1 | 1/2009 | Miyata et al. |
| 2011/0015618 | A1 | 1/2011 | Satou et al. |

FOREIGN PATENT DOCUMENTS

| JP | 6501179 T | 2/1994 |
| JP | 2005103171 A | 4/2005 |
| JP | 2006511304 T | 4/2006 |
| JP | 2006519068 | 8/2006 |
| JP | 2007503954 | 3/2007 |

(Continued)

OTHER PUBLICATIONS

Japanese Office Action for Application No. 2010-093858 mailed Jun. 8, 2012.

(Continued)

*Primary Examiner* — Max Hindenburg
(74) *Attorney, Agent, or Firm* — Lowe Hauptman & Ham, LLP

(57) ABSTRACT

An object of the present invention is to provide a guidewire having high safety and improved flexibility and rotation followability. This guidewire has an inner coil that surrounds a distal side portion of a core shaft, and an outer coil that surrounds the inner coil and the distal side portion of the core shaft. A front end of the outer coil and a front end of the inner coil are joined to a tip of the core shaft by a tip plug. Further, the guidewire has a coil joint that joins only the outer coil and the inner coil to each other. With this configuration, the flexibility of the inner coil is maintained. Moreover, rotation of a proximal side of the guidewire is transmitted to the inner coil not only from the core shaft but also from the outer coil. This leads to improvement in rotation followability.

4 Claims, 9 Drawing Sheets

(56) References Cited

FOREIGN PATENT DOCUMENTS

| | | |
|---|---|---|
| JP | 2008161491 A | 7/2008 |
| JP | 2009000337 | 1/2009 |
| WO | 2005035042 | 4/2005 |
| WO | 2009/119386 A1 | 10/2009 |

OTHER PUBLICATIONS

Office Action corresponding to JP2010-094730, dated May 10, 2012.
Japanese Office Action for JP2010-093858 issued Dec. 15, 2011.
Extended EP Search Report for EP10195980.7 dated Nov. 29, 2011.

* cited by examiner

GUIDEWIRE

CROSS REFERENCE TO RELATED APPLICATIONS

This application is based on Japanese Patent Application No. 2009-293660 filed with the Japan Patent Office on Dec. 25, 2009, No. 2010-093858 filed on Apr. 15, 2010, and No. 2010-094730 filed on Apr. 16, 2010, the entire content of which is hereby incorporated by reference.

TECHNICAL FIELD

The present invention relates to a medical guidewire.

BACKGROUND ART

There have conventionally been proposed a variety of medical guidewires for guiding, for example, a catheter which is used by being inserted into tubular organs such as blood vessels, digestive tracts, and ureters, and intracorporeal tissues for treatment or test. The guidewires include those with a structure where a double coil is provided at a distal portion of a core shaft (e.g., see Japanese Translation of PCT Publication Nos. 6-501179 and 2006-511304), and those using a stranded wire made up of a plurality of strands inside a coil (e.g., see Japanese Patent Application Laid-Open No. 2008-161491).

Generally, the guidewire is required to have flexibility on the front side (distal side) of the guidewire and rotation followability to transmit a rotation performed by an operator from the rear side (proximal side) to the front side of the guidewire.

SUMMARY OF INVENTION

In recent years, the area of use of the guidewire tends to be expanding. The guidewire has come to be used in more peripheral-side blood vessels in a heart, blood vessels in a brain, and the like. For this reason, the guidewire has been required to have higher safety, and further flexibility and rotation followability.

Especially, the blood vessel in the brain is a highly delicate portion. It is thereby required not only to prevent damage of the blood vessel and a tissue surrounding the vessel, but also to have high rotation followability.

The present invention has been made in view of such circumstances. An object of the present invention is to provide a guidewire having high safety and improved flexibility and rotation followability.

Moreover, the guidewire used for the blood vessel in the brain is required to have given stiffness for guiding a microcatheter, as well as the flexibility for preventing the inside of the blood vessel from being damaged. For enhancing the stiffness, typically, a diameter of a core shaft only needs to be increased. In this case, however, not only may the flexibility be lost, but also a distal shape formed by shaping may become difficult to retain while a restorability of the distal shape may deteriorate. Namely, at the time of using the guidewire, a conditioning called the shaping is often performed where a distal portion of the guidewire is bent by an operator such as a physician. When the diameter of the core shaft is increased with the aim of enhancing the stiffness of the core shaft, it becomes easier to perform the shaping. In this case, however, an angle formed by the shaping changes during the use inside a blood vessel, making it difficult to maintain that angle. Further, the distal portion of the core shaft is bent due to a load that acts on the guidewire inside a bent blood vessel, to have a residual angle without being restored.

The present invention has been made in view of such circumstances, and an object of the present invention is to provide a guidewire having sufficient stiffness for a guiding equipment such as a microcatheter, while being capable of retaining a distal shape formed by the shaping, and further having high restorability.

In the present invention, the above object is achieved by the structures listed below.

A guidewire in accordance with the present invention includes: a core shaft; an inner coil that is formed by winding at least one strand, and surrounds a distal side portion of the core shaft; an outer coil that is formed by winding at least one strand, and surrounds the inner coil and the distal side portion of the core shaft; a tip joint that joins a front end of the outer coil and a front end of the inner coil to a tip of the core shaft; an outer rear end joint that joins a rear end of the outer coil to the core shaft; an inner rear end joint that joins a rear end of the inner coil to the core shaft on a front side of the outer rear end joint; and a coil joint that is located between the tip joint and the inner rear end joint, and joins only the outer coil and the inner coil to each other.

Another guidewire in accordance with the present invention includes: a core shaft; an inner coil that is formed by stranding a plurality of strands, and surrounds a distal side portion of the core shaft; an outer coil that is formed by winding at least one strand, has an open coiled portion, on a front side of the outer coil, where coils are wound so as to be spaced from one another, while having a close coiled portion, on a rear side of the outer coil, where the strands are wound so as to come into substantially contact with one another, and surrounds the inner coil and the distal side portion of the core shaft; a tip joint that joins a front end of the outer coil and a front end of the inner coil to a tip of the core shaft; an outer rear end joint that joins a rear end of the outer coil to the core shaft; and an inner rear end joint that joins a rear end of the inner coil only to the core shaft on a rear side of the open coiled portion of the outer coil as well as on a front side of the outer rear end joint.

BRIEF DESCRIPTION OF DRAWINGS

The foregoing and other objects, features, aspects and advantages of the invention will become more apparent from the following detailed description when taken in conjunction with the accompanying drawings.

DESCRIPTION OF EMBODIMENTS

Figure 1:
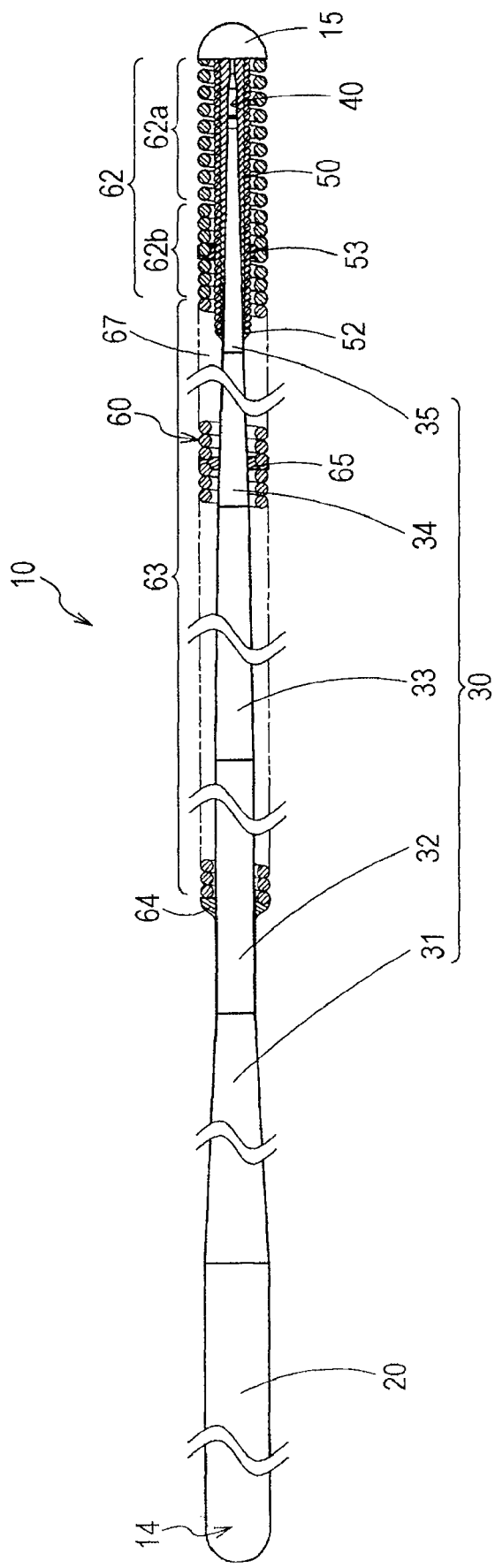
FIG. 1 illustrates an overall view of a guidewire of the present embodiment.
Figure 2:
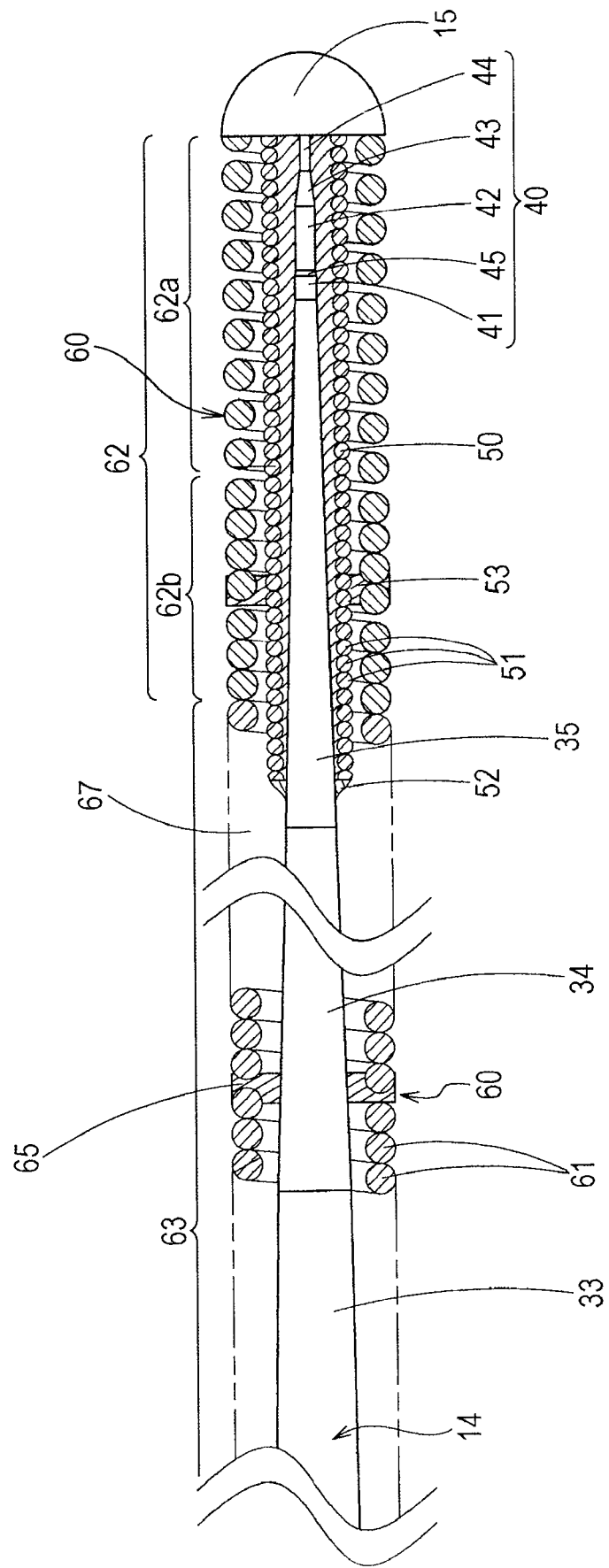
FIG. 2 illustrates a partially expanded view of FIG. 1.

<1> A guidewire in accordance with a first aspect of the invention includes: a core shaft; an inner coil that is formed by winding at least one strand, and surrounds a distal side portion of the core shaft; an outer coil that is formed by winding at least one strand, and surrounds the inner coil and the distal side portion of the core shaft; a tip joint that joins a front end of the outer coil and a front end of the inner coil to a tip of the core shaft; an outer rear end joint that joins a rear end of the outer coil to the core shaft; an inner rear end joint that joins a rear end of the inner coil to the core shaft on a front side of the outer rear end joint; and a coil joint that is located between the tip joint and the inner rear end joint, and joins only the outer coil and the inner coil to each other.

<2> A guidewire in accordance with a second aspect of the invention is the guidewire of the first aspect described above, wherein the outer coil has an open coiled portion, with coils of the strand spaced from one another, on a front side of the coil joint.

<3> A guidewire in accordance with a third aspect of the invention is the guidewire of the first aspect described above, wherein the outer coil has a close coiled portion, with coils of the strand are substantially in contact with one another on a rear side of the coil joint.

<4> A guidewire in accordance with a fourth aspect of the invention is the guidewire of the first aspect described above, wherein the outer coil has a radiopaque portion, made up of the strand of a radiopaque material, on a front end side of the outer coil while having a radiotransparent portion, made up of the strand of a radiolucent material, on a rear end side of the outer coil, the radiopaque portion has an open coiled portion, with coils of strand spaced from one another and wound in an open coiled manner, on a front end side of the radiopaque portion while having a close coiled portion, with coils of strand being substantially in contact with one another and wound in a close coiled manner, on a rear end side of the radiopaque portion, and the coil joint joins the outer coil with the inner coil in the close coiled portion of the radiopaque portion.

<5> A guidewire in accordance with a fifth aspect of the invention is the guidewire of the fourth aspect described above, wherein the radiotransparent portion is wound in a close coiled state where the coils of the strand are substantially in contact with one another.

<6> A guidewire in accordance with a sixth aspect of the invention is the guidewire of the first aspect described above, wherein the distal side portion of the core shaft is provided with a flat portion having at least two opposed plane portions.

<7> A guidewire in accordance with a seventh aspect of the invention is the guidewire of the first aspect described above, wherein the inner coil is a hollow stranded coil formed by stranding a plurality of strands.

<8> A guidewire in accordance with an eighth aspect of the invention includes: a core shaft; an inner coil that is formed by stranding a plurality of strands, and surrounds a distal side portion of the core shaft; an outer coil that is formed by winding at least one strand, has an open coiled portion, on a front side of the outer coil, where coils are wound so as to be spaced from one another, while having a close coiled portion, on a rear side of the outer coil, where the strands are wound so as to come into substantially contact with one another, and surrounds the inner coil and the distal side portion of the core shaft; a tip joint that joins a front end of the outer coil and a front end of the inner coil to a tip of the core shaft; an outer rear end joint that joins a rear end of the outer coil to the core shaft; and an inner rear end joint that joins a rear end of the inner coil only to the core shaft on a rear side of the open coiled portion of the outer coil as well as on a front side of the outer rear end joint.

<9> A guidewire in accordance with a ninth aspect of the invention is the guidewire of the eighth aspect described above, wherein the outer coil has a radiopaque portion, on a front end side of the outer coil, which is made up of strand of a radiopaque material and at least part of the front end side of which is the open coiled portion, while having a radiotransparent portion, on a rear end side of the outer coil, which is made up of strand of a radiolucent material and only includes the close coiled portion, and the inner rear end joint of the inner coil is located on a rear side of the radiopaque portion.

<10> A guidewire guidewire in accordance with a tenth aspect of the invention is the guidewire of the eighth aspect described above, wherein the outer coil has an outer intermediate joint that joins the outer coil to the core shaft in between the tip joint and the outer rear end joint, and the inner rear end joint of the inner coil is located on the front side of the outer intermediate joint.

<11> A guidewire in accordance with an eleventh aspect of the invention is the guidewire of the tenth aspect described above, wherein the outer intermediate joint of the outer coil is located in an intermediate taper part as a portion tapering toward the tip of the core shaft, the inner rear end joint of the inner coil is located in a front taper part, tapering toward the tip of the core shaft, located on a front side of the intermediate taper part, and an inclination angle of the intermediate taper part differs from an inclination angle of the front side taper part.

<12> A guidewire in accordance with a twelfth aspect of the invention is the guidewire of the eighth aspect described above, including a coil joint that joins only the outer coil and the inner coil to each other between the tip joint and the inner rear end joint of the inner coil.

<13> A guidewire in accordance with a thirteenth aspect of the invention is the guidewire of the twelfth aspect described above, wherein the outer coil is in a close coiled state where coils of the strand are substantially in contact with one another on a rear side of the coil joint.

<14> A guidewire in accordance with a fourteenth aspect of the invention is the guidewire of the eighth aspect described above, wherein the distal side portion of the core shaft surrounded by the inner coil has at least two cylindrical portions with different diameters, which are a large-diameter flexible part and a small-diameter flexible part with a diameter smaller than that of the large-diameter flexible part.

<15> A guidewire in accordance with a fifteenth aspect of the invention is the guidewire of the fourteenth aspect described above, wherein the small-diameter flexible part is disposed in a position corresponding to the open coiled portion of the outer coil.

<16> A guidewire in accordance with a sixteenth aspect of the invention is the guidewire of the eighth aspect described above, wherein the distal side portion of the core shaft is provided with a flat portion having at least two opposed plane portions.

<1> In the guidewire in accordance with the first aspect of the invention, the distal side portion of the guidewire is protected by a flexible coil portion having the double coil structure made up of the inner coil and the outer coil. With this flexible coil portion thus coming into contact with a blood vessel wall and the like in the body, damage of a blood vessel and the like can be prevented as much as possible.

Further, in the guidewire in accordance with the first aspect of the invention, the rotation followability is improved by the inner coil. Moreover, with the outer coil and the inner coil joined to each other by the coil joint, rotation applied from the proximal side of the core shaft can also be transmitted from the outer coil to the inner coil. Therefore, the rotation followability is further improved.

Furthermore, the coil joint only joins the outer coil and the inner coil to each other, and does not join the core shaft to the coil. Therefore, deterioration in flexibility of the inner coil and the outer coil can be prevented as much as possible, so as to maintain the safety.

<2> In the second aspect of the invention, the outer coil has the open coiled portion, with coils of the strand spaced from one another, on the front side of the coil joint. This leads to further improvement in flexibility of the tip portion of the guidewire. It is thus possible to further prevent damage of the blood vessel and the like in the body.

<3> In the third aspect of the invention, the outer coil is in the close coiled portion, with coils of the strand are in substantially contact with one another on the rear side of the coil joint. Therefore, when rotation applied from the proximal side of the core shaft is transmitted from the outer coil to the inner coil, loss of the transmission of the rotation due to the presence of spaces among the coils of the strand can be prevented as much as possible. This leads to further improvement in rotation followability.

<4> In the fourth aspect of the invention, the stiffness increases in the order of the open coiled portion, which is made of the radiopaque material, of the radiopaque portion, the close coiled portion of this radiopaque portion, and the radiotransparent portion made of the radiolucent material. Therefore, the guidewire has a structure with higher flexibility and safety toward the tip.

Further, the coil joint is located in the close coiled portion of the radiopaque portion which has intermediate stiffness. Therefore, the abrupt stiffness change of the guidewire is prevented as much as possible. This can improve rotation followability and pushability of the guidewire.

<5> In the fifth aspect of the invention, strand on the rear side of the coil joint are all wound in a close coiled manner. Therefore, when rotation applied from the proximal side of the core shaft is transmitted from the outer coil to the inner coil, loss of the transmission of the rotation due to the presence of spaces among the coils of the strand can be prevented as much as possible. This leads to further improvement in rotation followability.

<6> In the sixth aspect of the invention, the distal side portion of the core shaft is provided with the flat portion, thereby to give high torsional stiffness. This makes it easy for the guidewire to change a direction of a catheter. Further, at the time of performing such an operation, a load may act on a boundary with the flat portion. However, with the inner coil provided, the load is also shared by the inner coil. Accordingly, bending or kinking of the core shaft can be prevented as much as possible.

<7> In the seventh aspect of the invention, the inner coil is a hollow stranded coil formed by stranding a plurality of strands. The inner coil thus has a structure with high rotation torque transmissibility as well as flexibility. Hence this can lead to further improvement in rotation followability.

<8> In the guidewire of the eighth aspect of the invention, the tip portion of the guidewire is protected by the double coil structure made up of the outer coil and the inner coil formed by stranding a plurality of strands. In this double coil structure, the outer coil has the open coiled portion on the front side. This can lead to improvement in flexibility of the tip portion of the guidewire. Since the structure has the open coiled portion added to the double coil structure, the flexible coil portion in the guidewire comes into contact with the blood vessel wall and the like in the body. Hence damage of the blood vessel and the like can be prevented as much as possible.

Further, the rotation followability and pushability of the guidewire of the eighth aspect can be improved by the inner coil made up of stranded wires. Moreover, in this guidewire, the inner rear end joint of the inner coil is not joined to the outer coil, but joined only to the core shaft. Furthermore, this inner rear end joint is disposed on the rear side of the boundary between the open coiled portion and the close coiled portion of the outer coil. With this configuration, it is possible to make the inner rear end joint of the inner coil as small as possible, so as to prevent a change in stiffness of the core shaft as much as possible. It is further possible to prevent concentration of the change in stiffness which is generated on the boundary between the open coiled portion and the close coiled portion of the outer coil, and the change in stiffness of the core shaft which is generated due to the inner rear joint of the inner coil. This can prevent the abrupt stiffness change of the tip portion of the guidewire. Therefore, loss of torque transmission applied from the proximal side to the distal side in the guidewire can be prevented as much as possible. This can lead to further improvement in rotation followability and pushability of the guidewire.

Further, in the guidewire of the eighth aspect, the stiffness of the tip portion of the core shaft can be ensured by the inner coil. Therefore, even when a diameter of the portion surrounded by the inner coil in the distal side portion of the core shaft is decreased, sufficient stiffness for guiding the catheter can be provided. Further, with diameters of the inner coil and the core shaft decreased, even if an angle formed by shaping changes in a case where the tip portion of the guidewire in a shaped state is inserted into the blood vessel and the like in the body, the tip portion of the guidewire can be restored without being plastically deformed, so as to maintain the angle formed by shaping. Moreover, even when an external force acts on the distal side portion of the guidewire due to a tortuous blood vessel and the like, plastic deformation of this tip portion can be prevented as much as possible. Namely, restoring force of this tip portion can be improved.

Further, with the outer coil having the open coiled portion on the front side, even when the guidewire is formed to have the double coil structure, the shaping thereof can be performed with ease.

<9> In the ninth aspect of the invention, the stiffness increases in the order of the open coiled portion, which is made of the radiopaque material, of the radiopaque portion, the close coiled portion of this radiopaque portion, and the radiotransparent portion made of the radiolucent material and made up only of the close coiled portion. Therefore, the guidewire has a structure with higher flexibility and safety toward the tip.

Further, the inner rear end joint of the inner coil is disposed on not only the rear side of the boundary between the open coiled portion and the close coiled portion, but also the rear side of the boundary between the radiopaque portion and the radiotransparent portion. It is thus possible to prevent concentration of the change in stiffness which is generated on each boundary, and the change in stiffness of the core shaft which is generated due to the inner rear end joint of the inner coil. Hence it is possible to prevent the abrupt stiffness change of the tip portion of the guidewire. This can lead to further improvement in rotation followability and pushability of the guidewire.

<10> In the tenth aspect of the invention, the inner rear end joint of the inner coil is located on the front side of the outer intermediate joint, and is not joined to the outer intermediate joint. Thereby, the abrupt stiffness change of the guidewire can be prevented as much as possible. For this reason, torque and pushing force applied from the proximal side of the guidewire can be efficiently transmitted to the distal side. This can lead to improvement in torque transmissibility.

<11> In the eleventh aspect of the invention, there is a difference in inclination angle between the intermediate taper part where the outer intermediate joint of the outer coil is located and the front taper part where the inner rear end joint of the inner coil is located. Namely, there is a change in inclination of the taper angle between the intermediate taper part where no inner coil is present and the front taper part where the inner coil is present. Such a change in inclination in the intermediate taper part offsets an increase in stiffness due to the inner coil as much as possible. Therefore, an abrupt change in stiffness of the guidewire, caused by disposing the inner coil in the tip portion of the core shaft, can be prevented. This can lead to further improvement in rotation followability and pushability of the guidewire.

<12> In the twelfth aspect of the invention, the rotation followability is improved due to the inner coil. Further, in this aspect, the outer coil and the inner coil are joined to each other by the coil joint. Therefore, rotation applied from the proximal side of the core shaft can also be transmitted from the outer coil to the inner coil. This leads to further improvement in rotation followability.

Moreover, the coil joint only joins the outer coil and the inner coil to each other, and is not joined to the core shaft. Therefore, deterioration in flexibility of the inner coil and the outer coil can be prevented as much as possible, so as to maintain the safety.

<13> In the thirteenth aspect of the invention, the outer coil is in a close coiled state where the coils of the strand are in substantially contact with one another on the rear side of the coil joint. Therefore, when rotation applied from the proximal side of the core shaft is transmitted from the outer coil to the inner coil, loss of the transmission of the rotation due to the presence of spaces among the coils of the strand can be prevented as much as possible. This leads to further improvement in rotation followability.

<14> In the fourteenth aspect of the invention, the distal side portion of the core shaft located inside the inner coil is divided into at least two portions with different stiffness, including a large-diameter flexible part and a small-diameter flexible part, and the diameters are then reduced. It is thus possible to modulate the change in stiffness of the core shaft. Further, it is possible to simultaneously achieve the reduction in diameter for improving retention characteristics and restorability of the distal shape angled by shaping and the ensuring of the stiffness for favorably guiding equipment such as a microcatheter.

Namely, providing the inner coil allows reduction in diameter of the tip portion of the core shaft. This contributes to the retention characteristics and the restorability of the distal shape. On the contrary, when the range of the reduced diameter is made excessively long, it is disadvantageous in ensuring the stiffness for guiding the equipment such as the microcatheter. Hence these characteristics can be simultaneously achieved by also changing the stiffness in a gradual manner inside the inner coil.

<15> In the fifteenth aspect of the invention, the small-diameter flexible part of the tip portion of the core shaft is disposed in a position corresponding to the open coiled portion of the outer coil. In this portion, with the outer coil being the open coiled portion, the tip portion of the guidewire is easy to bend even with the inner coil. It thus becomes easy for an operator to shape this tip portion with a reduced diameter.

<16> In the sixteenth aspect of the invention, the distal side portion of the core shaft is provided with the flat portion, thereby to give high torsional stiffness. This makes it easy for the guidewire to change the direction of a catheter. Further, at the time of performing such an operation, a load may act on a boundary with the flat portion. However, with the inner coil provided, the load is also shared by the inner coil. Accordingly, bend or kink of the core shaft can be prevented as much as possible.

The guidewire of the present embodiment will be described with reference to FIGS. 1 to 4. In FIGS. 1 to 4, the right side is the front side (distal side) that is inserted into a body, and the left side is the rear side (base end side, proximal side) that is operated by an operator.

A guidewire 10 is used for treatment of a blood vessel in a brain. The guidewire 10, for example, has a length of about 2000 mm in the case of the present embodiment.

The guidewire 10 mainly includes a core shaft 14, an inner coil 50 and an outer coil 60. The core shaft 14 is roughly divided into a body portion 20, a distal portion 30 and a most distal portion 40. The outer surface of the guidewire 10 from the tip to a predetermined length of the body portion 20 through the outer coil 60 has been subjected to hydrophilic coating.

The distal portion 30 and the most distal portion 40 are portions with a reduced diameter of the core shaft 14, and a total axial length of the both portions is about 420 mm in the present embodiment. The body portion 20 is a portion in cylindrical shape with a given diameter, and takes up the portion other than the distal portion 30 and the most distal portion 40. In the present embodiment, the diameter of the body portion 20 is set to about 0.33 mm.

A material for the core shaft 14 is not particularly limited, but in the case of the present embodiment, stainless steel (SUS304) is used. As the material other than this, a super elastic alloy such as Ni—Ti alloy, a piano wire, or the like may be used.

In the distal portion 30, a first taper part 31, a first small-diameter part 32, a second taper part 33, a third taper part (intermediate taper part) 34, and a fourth taper part (front taper part) 35 are provided in this order from the body portion 20 side toward the most distal portion 40. In the present embodiment, the axial lengths of the first taper part 31 and the first small-diameter part 32 are each about 100 mm.

The first taper part 31 is a tapered portion having a circular cross section. In the present embodiment, a diameter of the first taper part 31 decreases from about 0.33 mm to about 0.20 mm toward a distal direction.

The first small-diameter part 32 is a cylindrical portion having a circular cross section and a given diameter, which is about 0.20 mm in the present embodiment.

The second taper part 33, the third taper part 34 and the fourth taper part 35 are each a tapered portion having a different inclination angle and a circular cross section. In the present embodiment, a total axial length of the second taper part 33, the third taper part 34 and the fourth taper part 35 is about 205 mm. Further, the diameter from the proximal end of the second taper part 33 to a distal end of the fourth taper part 35 is set to decrease from about 0.20 mm to about 0.05 mm.

A cylindrical portion having a given diameter can also be provided among the respective taper parts 33, 34 and 35 as necessary. Further, the number of taper parts and an angle of the taper can also be set as appropriate.

The most distal portion 40 is provided with a large-diameter flexible part 41, a small-diameter flexible part 42, a first flat part 43 and a second flat part 44 in this order from the distal portion 30 side toward the tip. In the present embodiment, the axial length of the most distal portion 40 is about 15 mm.

The large-diameter flexible part 41 and the small-diameter flexible part 42 are cylindrical portions each having a circular cross section and a given diameter. The diameter of the small-diameter flexible part 42 is set smaller than that of the large-diameter flexible part 41. The small-diameter flexible part 42 and the large-diameter flexible part 41 are connected to each other by a minute taper part 45 provided therebetween.

As described above, decreasing the diameter of the most distal portion 40 located inside the inner coil 50 by dividing the most distal portion 40 into the small-diameter flexible part 42 and the large-diameter flexible part 41 can moderate a change in stiffness of the core shaft 14. Further, this also allows a balance between the reduction in diameter for improving retention characteristics and restorability of the distal shape angled by the shaping and the ensuring of the stiffness for favorably guiding the equipment such as the microcatheter.

Namely, providing the inner coil 50 allows reduction in diameter of the most distal portion 40. This contributes to the retention characteristics and the restorability of the distal shape by the shaping. On the contrary, when the length of the reduced diameter is made excessively long, it is disadvantageous in ensuring the stiffness for guiding the equipment such as the microcatheter. Hence these characteristics can be balanced by also changing the stiffness in a gradual manner inside the inner coil 50.

Figure 3:
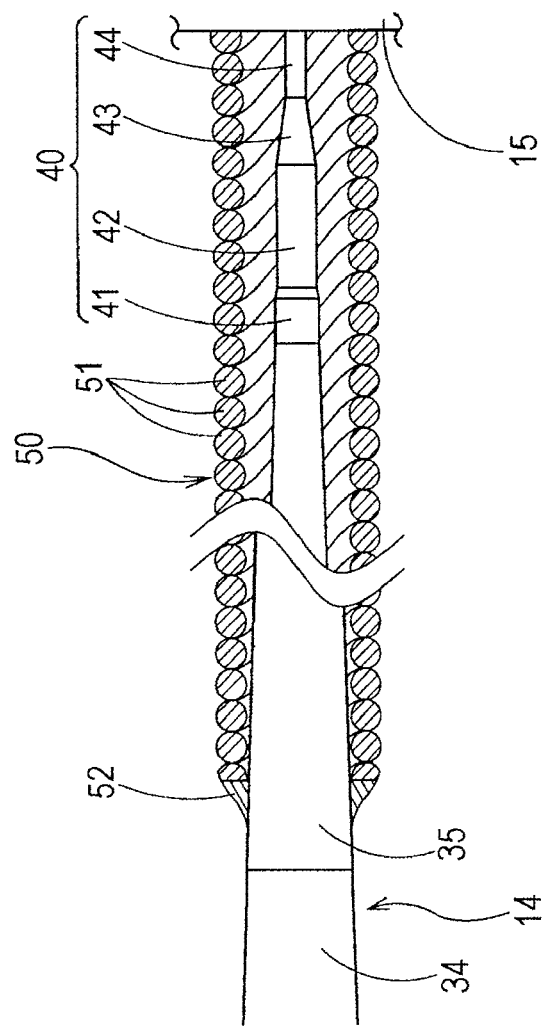
FIG. 3 illustrates a view of a most distal portion of the guidewire of the present embodiment.
Figure 4:
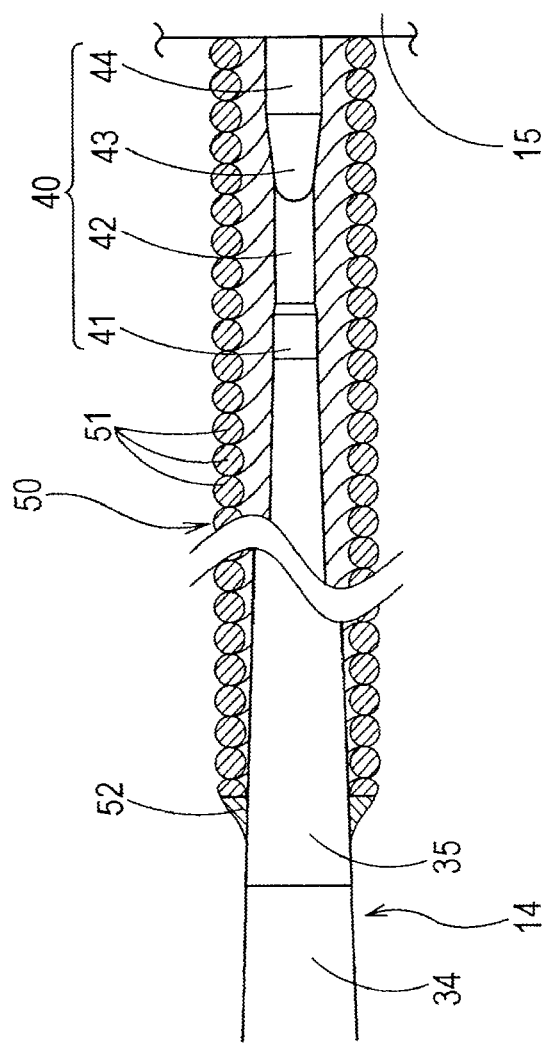
FIG. 4 illustrates a top view of FIG. 3.

The first flat part 43 and the second flat part 44 are portions molded by pressing a cylindrical portion continued from the small-diameter flexible part 42. As illustrated in FIGS. 3 and 4, the first flat part 43 is a tapered portion having a pair of inclined planes with a width increasing, and a thickness in a height decreasing, from the small-diameter flexible part 42 toward the tip side. This first flat part 43 is connected with the second flat part 44 as a flat portion having a substantially rectangular cross section.

The first flat part 43 is provided for modulating a change in stiffness in order to prevent concentration of stress due to an increased change in stiffness between the small-diameter flexible part 42 and the second flat part 44. In the case of the present embodiment, the axial length of the first flat part 43 is about 3.0 mm, so that a sufficiently moderate change in stiffness can be obtained.

As illustrated in FIGS. 3 and 4, the second flat part 44 is a substantially rectangular plate-like portion, and has two pairs of planes substantially parallel to the axis line of the core shaft 14. The axial length of the second flat part 44 is set substantially the same as the axial length of the first flat part 43. This length is about 3.0 mm in the case of the present embodiment. The width of the second flat part 44 expanded in flat shape ensures a predetermined space between the side surface of the second flat part 44 and the inner peripheral surface of the inner coil 50, as illustrated in FIG. 4. However, the side surface of the second flat part 44 may come into contact with the inner peripheral surface of the inner coil 50.

It is to be noted that the second flat part 44 is molded by pressing. For this reason, the side surface of the second flat part 44 is not plane but arc-like in a precise sense. Accordingly, the second flat part 44 having a substantially rectangular cross section includes such a shape with an arc-like side surface.

A total axial length of the first flat part 43 and the second flat part 44 is preferably set to the range of about 2.0 mm to about 10.0 mm. Of the two flat parts, the second flat part 44 constituting the most flexible portion of the core shaft 14 preferably takes up about 1.0 mm or longer.

The flattened portion constituted by the first flat part 43 and the second flat part 44 enhances the torsional stiffness of the tip portion, i.e. the most distal portion 40, of the guidewire 10, as well as making the tip portion more flexible. Further, this flattened portion is also used to angle and direct the tip portion of the guidewire 10, which is called shaping. Herein, shaping would be difficult when this flattened portion is shorter than about 2.0 mm.

Further, as the microcatheter into which the guidewire 10 is inserted, there is often used one having an angled portion at a portion about 8.0 mm from the tip of the catheter. When a total axial length of the first flat part 43 and the second flat part 44 is larger than about 10.0 mm, the flattened portion may be present over the angled portion of the catheter. In such a state, the tip portion of the guidewire 10 is stucked on the front side of the angled portion of the microcatheter. For this reason, when rotational torque is applied from the proximal side of the guidewire 10, torsional stress acts on the guidewire in the stucked angled portion. Further, when further rotational torque is applied and the torsional stress exceeds a given amount, a phenomenon called "whip" may be likely to occur in which the stucked tip portion of the guidewire 10 suddenly moves greatly in a rotating direction to release the torsional stress.

The most distal portion 40 and most of the fourth taper part 35 of the distal portion 30 are inserted through the inside of the inner 50. The inner coil 50 is a hollow stranded coil manufactured by stranding a plurality of metal strands 51 on a core, removing residual stress at the time of the stranding by known thermal treatment, and then pulling out the core. In the case of the present embodiment, an outer diameter of the inner coil 50 is about 0.19 mm. Further, the axial length of the inner coil 50 is about 55.0 mm.

Six strands 51 are used for the inner coil 50. A diameter of the strand 51 is about 0.035 mm. A pitch (axial distance defined by one spiral formed by one strand makes a round) of the inner coil 50 is set to be in the range of about 0.25 mm to about 0.29 mm. The number of strands 51 and the diameter thereof are determined as appropriate in view of an outer diameter and stiffness required for the inner coil 50, and are not limited to the above values.

Although a material for the strands 51 is not particularly limited, in the case of the present embodiment, stainless steel is employed. As a material other than this, a super elastic alloy such as an Ni—Ti alloy is used. Further, strands made of different materials may also be combined.

The front end of the inner coil 50 is joined by brazing to the tip of the core shaft 14 with the axial line of the core shaft 14 at the center, with the front end of the outer coil 60. This brazed portion forms a substantially hemispherical tip plug (tip joint) 15. The rear end of the inner coil 50 is joined by brazing to the fourth taper part 35 of the distal portion 30. This brazed portion forms an inner rear end joint 52.

The inner coil 50 surrounds most of the fourth taper part 35 of the core shaft 14. The inclination angles are different between the third taper part (intermediate taper part) 34 unenclosed by the inner coil 50 and the fourth taper part (front taper part) 35 enclosed by the inner coil 50. This is designed for the purpose of preventing a sudden change in stiffness of the guidewire 10, which is caused by disposing the inner coil 50. Namely, changing the inclination of the fourth taper part 35 of the core shaft 14 offsets an increase in stiffness due to the inner coil 50 as much as possible.

Namely, the angle of the third taper part 34 with respect to the axial line of the core shaft 14 is larger than the angle of the fourth taper part 35. Thereby, a rate of change in diameter is increased in the third taper part 34, so as to offset the decrease in stiffness due to the third taper part 34 having no inner coil 50.

Further, the inner rear end joint 52 of the inner coil 50 is jointed only to the core shaft 14, and is not joined to a later-mentioned outer intermediate joint 65 of the outer coil 60, and the like. This can make the brazed portion as small as possible. Therefore, the change in stiffness of the core shaft 14 due to brazing can be reduced as much as possible.

It is to be noted that in cases where another taper part having a further different angle can be placed between the third taper part 34 and the fourth taper part 35, where the stiffness of the outer coil 60 changes due to a change in diameter of the outer coil 60 or diameter of the strand, or in some other cases, the angle of the third taper part 34 having the outer intermediate joint 65 may be made smaller than the angle of the fourth taper part 35 having the inner coil 50. This may allow adjustment of the amount of change in stiffness.

Most of the portion from the most distal portion 40 to the first small-diameter part 32 of the distal portion 30, including the inner coil 50, is inserted through the inside of the outer coil 60. The outer coil 60 is formed by winding one metal strand 61. In the case of the present embodiment, an outer diameter of the outer coil 60 is about 0.36 mm. Further, the axial length of the outer coil 60 is about 300.0 mm.

The strand 61 of the outer coil 60 is one strand formed by joining a radiopaque metal wire such as platinum alloy with a radiolucent metal wire such as stainless steel. In the case of the present embodiment, a diameter of the strand 61 is about 0.065 mm. Therefore, in the case of the present embodiment, there is a space of about 0.02 mm in a radial direction between the inner peripheral surface of the outer coil 60 and the outer peripheral surface of the inner coil 50.

The outer coil 60 is formed of one strand. Since a pitch of the outer coil 60 can thereby be approximated to the diameter of the strand, the pitch is about 0.065 mm. On the other hand, the pitch of the inner coil 50 is set to the range of about 0.25 mm to about 0.29 mm as described above. Consequently, an average distance between adjacent coils of the six strands constituting the inner coil 50 is in the range of about 0.042 mm to about 0.048 mm. Hence the average distance between the adjacent coils of the strands of the inner coil 50 is set smaller than the average distance between the adjacent coils of the single strand of the outer coil 60.

In this manner, the inner coil 50 and the outer coil 60 are independent from each other with a space therebetween. The average distance between the adjacent coils of the strands of the inner coil 50 is set smaller than the average distance between the adjacent coils of the single strand of the outer coil 60. This makes the double coil coli structure made up of the inner coil 50 and the outer coil 60 easy to bend and flexible.

The portion of the outer coil 60 which is made of the radiopaque metal wire is a portion about 50.0 mm from the front end of the outer coil 60, and constitutes a radiopaque portion 62 that functions as a marker. In the radiopaque portion 62, a portion about 30.0 mm from the front end of the outer coil 60 is an open coiled portion 62*a* with the coils of the strand 61 wound in an open coiled manner so as to form a space therebetween. A portion in the rear side of the open coiled portion 62*a* is a close coiled portion 62*b* with the coils of the strand 61 wound in a close coiled manner so as to come into substantially contact with one another without a space therebetween. The space between coils of the strand 61 in the open coiled portion 62*a* is about 0.01 mm to about 0.02 mm.

The portion made up of the radiolucent metal wire takes up the portion of the outer coil 60 which is on the rear side of the radiopaque portion 62, and is the radiotransparent portion 63 where coils of the strand 61 are wound in the close coiled manner so as to come into substantially contact with one another.

The open coiled portion 62*a* of the outer coil 60 also contributes to facilitating the shaping of the tip portion of the guidewire 10. Namely, the double coil structure made up of the inner coil 50 and the outer coil 60 may give an operator an impression that it is more difficult to shape than a structure made up only of the outer coil and the core shaft for the reason of the coils interfering with each other at the time of performing the shaping, or for some other reason. However, providing the space between coils of the strand 61 in the outer coil 60 can make the structure easy to shape.

Therefore, the most distal portion 40 of the core shaft 14 is located in the open coiled portion 62*a*. In the most distal portion 40, the small-diameter flexible part 42, the first flat part 43 and the second flat part 44, which have a high probability of being shaped, are preferably located in the open coiled portion 62*a*.

The front end of the outer coil 60 is joined by brazing to the tip of the core shaft 14 in the tip plug 15, coaxially with the inner coil 50. The rear end of the outer coil 60 is joined by brazing to the first small-diameter part 32 of the distal portion 30. This brazed portion forms an outer rear end joint 64.

Further, the outer coil 60 is joined by brazing to the third taper part 34 of the distal portion 30. This brazed portion forms the outer intermediate joint 65.

The outer coil 60 and the inner coil 50 are joined to each other by brazing in a coil joint 53. The coil joint 53 serves to join only the outer coil 60 and the inner coil 50 to each other. The material for brazing does not reach the core shaft 14, so the inner coil 50 and the core shaft 14 are not joined by the coil joint 53.

The coil joint 53 is located on the rear side of the open coiled portion 62*a* with the strand 61 wound in the open coiled manner in the radiopaque portion 62 of the outer coil 60, and disposed substantially at the center of the close coiled portion 62*b* with the strand 61 wound in the close coiled manner. The reason for this is to prevent, as much as possible, an abrupt change in stiffness of the guidewire 10 due to the coil joint 53. Namely, in the outer coil 60, the radiopaque portion 62 made up of the radiopaque metal wires such as the platinum alloy has low stiffness as compared with the radiotransparent portion 63 made up of the radiolucent metal wires such as the stainless steel because of the difference in material therebetween. Further, in using the same material, the open coiled portion 62*a* with the coils of the strand 61 having a space therebetween has lower stiffness than the close coiled portion 62*b*. Accordingly, the open coiled portion 62*a* has the lowest stiffness (is most flexible), the close coiled portion 62*b* has the second lowest stiffness, and the radiotransparent portion 63 with the radiolucent strand 61 wound in the close coiled manner has the highest stiffness. If the boundaries of the portions 62*a*, 62*b* and 63 that occur stiffness change are gathered at the coil joint 53, the change in stiffness is further emphasized. Therefore, the above arrangement has been adopted for preventing such emphasized stiffness change as much as possible.

Similarly, the inner rear end joint 52 of the inner coil 50 described above is also disposed on the rear side of the radiopaque portion 62 of the outer coil 60 so as not to be gathered at the boundaries of the portions 62*a*, 62*b* and 63 where the change in stiffness occurs.

Further, the close coiled portion 62*b* of the radiopaque portion 62 and the radiotransparent portion 63, which are located on the rear side of the coil joint 53, are both made up of the close coiled manner of the strand 61. Rotational torque on the proximal side of the guidewire 10 is transmitted to the inner coil 50 not only from the core shaft 14 but also from the outer coil 60 through the coil joint 53. In the above configuration, the strand 61 is closely wound, thereby to prevent loss of transmission of the rotational torque.

Further, the inner rear end joint 52 of the inner coil 50 is disposed as spaced in an axial direction from the outer intermediate joint 65 of the outer coil 60. A space 67 is thereby formed. If the inner coil 50 and the outer coil 60 are joined to the core shaft 14 at the same position, the stiffness of the guidewire 10 becomes high at that position. This causes an abrupt change in stiffness of the guidewire 10. The space 67 serves to prevent such a change in stiffness as much as possible. By locating the joined portions of the rear end of the inner coil 50 and the intermediate portion of the outer coil 60 apart from each other, the material for brazing which is used for joining can be reduced. This can minimize an influence of the stiffness change that acts on the core shaft 14. Therefore, with this configuration, it is possible to improve transmissibility of the torque and pressing force applied from the proximal side of the guidewire 10.

Figure 5:
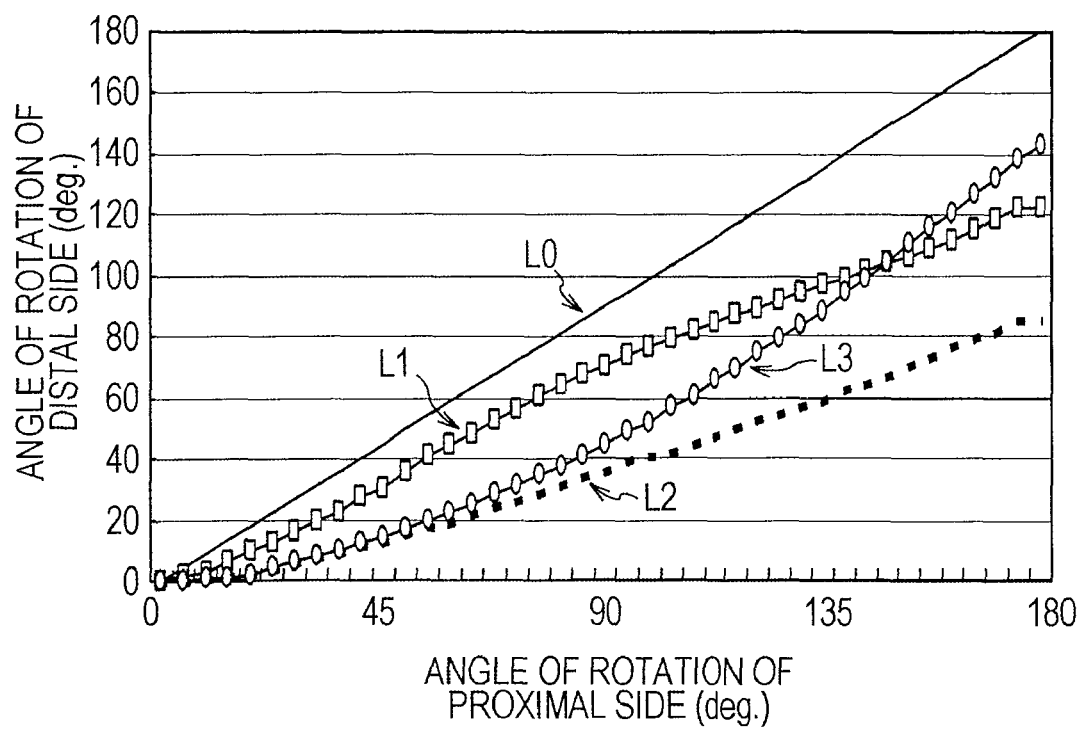
FIG. 5 illustrates a graph of rotation followability of the guidewire of the present embodiment.
Figure 6:
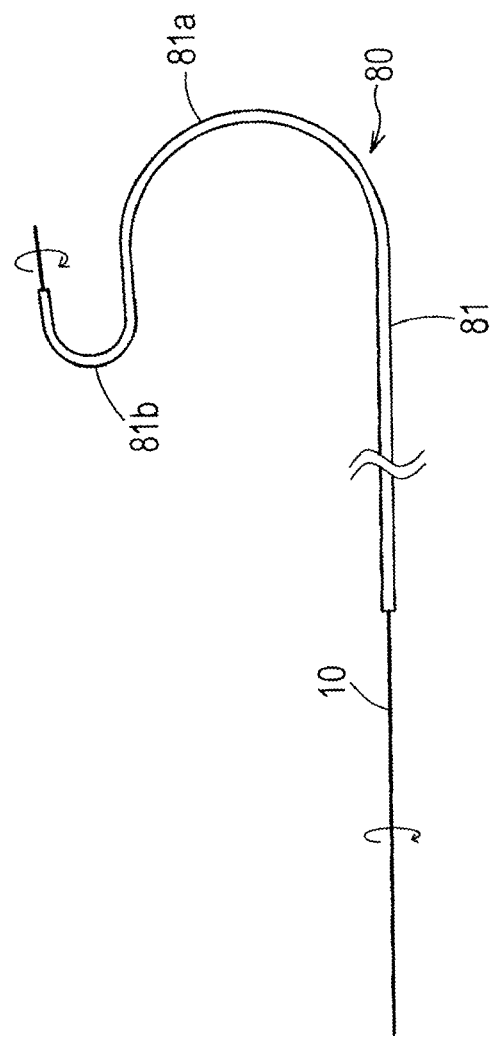
FIG. 6 illustrates a view of a data measurement device of FIG. 5.

For the sake of comparison, the guidewire 10 illustrated in FIGS. 1 to 4 and a guidewire for a comparison test were produced. The rotation followability of each guidewire was then measured using a measurement device 80 illustrated in FIG. 6. A graph illustrated in FIG. 5 shows a result of this measurement. Namely, this graph shows a result of measuring an angle of rotation of the distal side in the case of rotating the proximal side of the guidewire.

The measurement device 80 is formed in a model of a microcatheter that is used simultaneously with the guidewire 10 of the present embodiment, and made up of a resin-made tube 81 having a lumen inside. The tube 81 has a first curved portion 81a with a curvature radius of 60.0 mm on the rear side, and also has a second curved portion 81b with a curvature radius of 10.0 mm on the front side. Inside the measurement device 80 with this configuration, each of the guidewires produced for test, such as the guidewire 10, was inserted. The proximal side of each of those was then rotated clockwise by a predetermined angle [degree] up to 180 degrees, and an angle [degree] of rotation on the distal side at that time was measured.

In FIG. 5, a graph L0 indicated by a solid line indicates an ideal line for a guidewire with the proximal side and the distal side thereof rotated in the relation of 1:1. A graph L1 indicated using white rectangles is a measurement result of the guidewire 10 of the present embodiment. A graph L2 indicated using a broken line is a measurement result of a first comparative guidewire with a configuration of the guidewire 10 of the present embodiment without the inner coil 50. A graph L3 indicated using white circles is a measurement result of a second comparative guidewire with a configuration of the guidewire 10 of the present embodiment only without the coil joint 53 that joins the outer coil 60 and the inner coil 50 to each other.

The guidewire 10 of the present embodiment is aimed, for example, at the use for blood vessel in a brain. It was found as a result of a study conducted by the present inventors that in the case of being used with the aim as described above, the guidewire is often subjected to the rotating manipulation in the range near 0 to 90 degrees, and the rotation followability in this range is particularly important. For example, in the case of using the guidewire for the brain, at the time of the guidewire entering the inside of a target aneurysm, a highly accurate rotating manipulation is required in the range near 0 to 90 degrees for directing the tip of the guidewire to an opening of the aneurysm.

In FIG. 5, the graph L2 for the first comparative guidewire without the inner coil 50 is far off the ideal graph L0 not only in the range near 0 to 90 degrees but also in the range up to 180 degrees.

As indicated in the graph L3, the second comparative guidewire, provided with the inner coil 50 but without the coil joint 53, has the inner coil 50, and the rotation followability is thereby improved more than the first comparative guidewire. However, it is far off the ideal graph L0 in the range near 0 to 90 degrees. Namely, this graph L3 indicates that, when the operator rotates the proximal side of the guidewire, the distal side is not immediately rotated despite transmission of the rotation by the inner coil 50, and the second comparative guidewire thus has inferior operability since a considerable amount of additional rotation of the proximal side is required to obtain a desired amount of rotation of the distal side.

On the contrary, as indicated in the graph L1, it is found that the guidewire 10 of the present embodiment has the rotation followability slightly inferior to that of the second comparative guidewire in the range after about 130 degrees, but has the rotation followability close to that of the ideal graph L0 in the range near 0 to 90 degrees. Namely, in this guidewire 10, the distal side is immediately rotated when the operator rotates the proximal side. Hence the graph L1 indicates that the guidewire 10 has good operability. As described above, it is considered that the factor of improvement in rotation followability of the inner coil 50 is that the rotation from the proximal side of the guidewire 10 to the inner coil 50 is transmitted not only from the core shaft 14 but also from the outer coil 60 through the coil joint 53.

Further produced were the guidewire 10 illustrated in FIGS. 1 to 4, and comparative guidewires A and B which are different from the foregoing ones used for the test of FIG. 5. A comparison test was then conducted concerning the retention characteristics of the shaping angle and the restorability of the guidewire 10 of the present embodiment. Graph illustrated in FIGS. 7 and 8 are results of this test.

The comparative guidewire A has a configuration formed simply by removing the inner coil 50 from the configuration of the guidewire 10 of the present embodiment. The stiffness of the comparative guidewire A is thus lower than that of the guidewire 10 of the present embodiment.

The comparative guidewire B is not provided with the inner coil 50. However, the comparative guidewire B was produced such that the stiffness of the guidewire in the range of about 5 to 20 mm of its tip, which is important for the guidewire to guide the microcatheter or the like, is substantially the same value as that of the guidewire 10 (namely, such that substantially the same stiffness curve is given). To realize such stiffness, as compared with diameters of the large-diameter flexible part 41 and the small-diameter flexible part 42 of the guidewire 10, diameters of portions of the comparative guidewire B which correspond to the above-mentioned flexible parts are each set larger by about 1.2%

Figure 7:
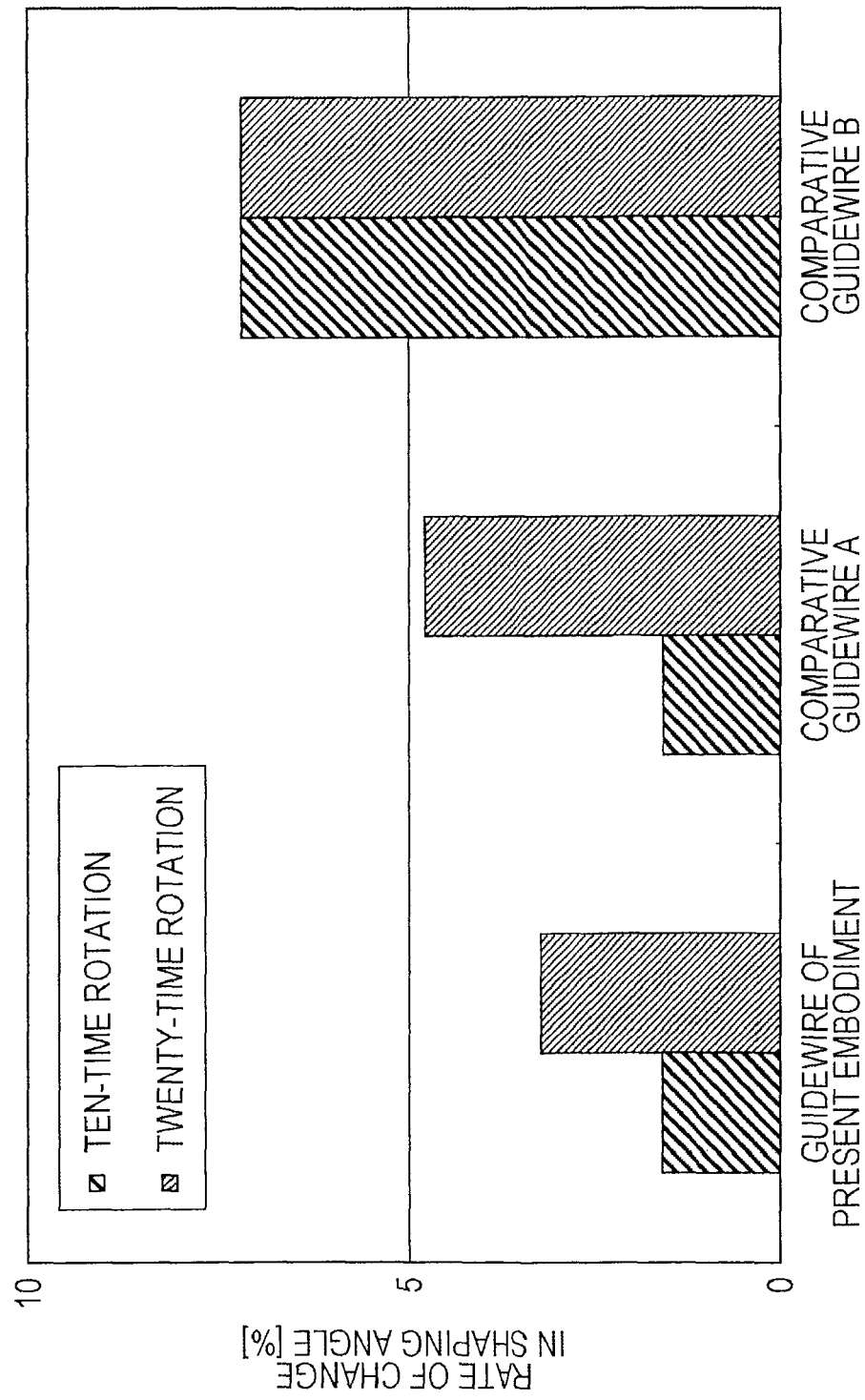
FIG. 7 illustrates a comparative graph of retention characteristics of the shaping angle of the guidewire of the present embodiment.
Figure 8:
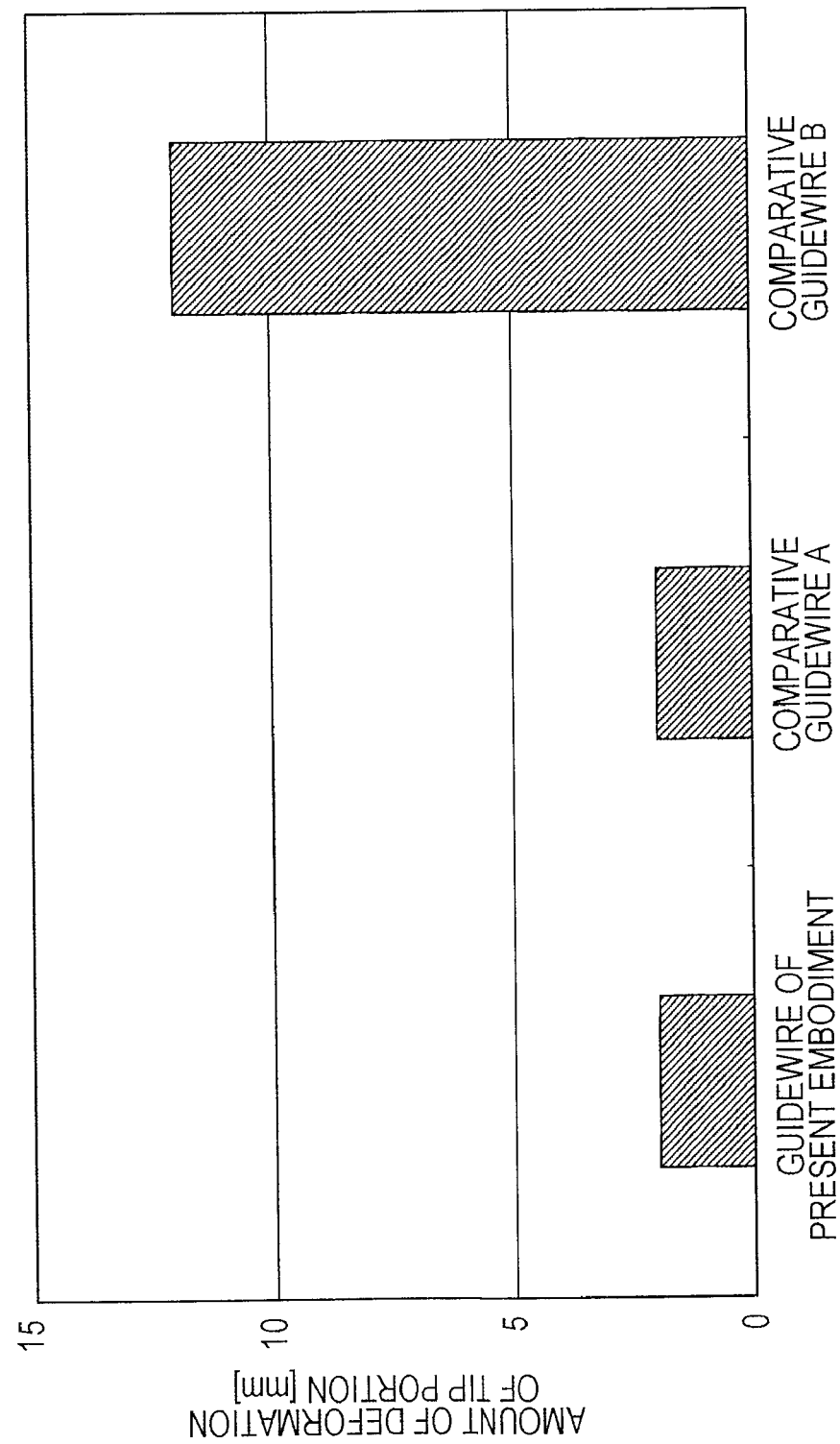
FIG. 8 illustrates a comparative graph of restorability of the guidewire of the present embodiment.

FIG. 7 illustrates a graph showing a result of the test comparing the retention characteristics of the shaping angle of the guidewire 10 of the present embodiment and the comparative guidewires A and B. Shaping is performed generally on the range of the second flat part 44 to the fourth taper part 35 where the inner coil 50 is provided. In this test, based on a result of empirical assumption of a portion with a high probability of being shaped, each guidewire was bent at a portion (corresponding to the small-diameter flexible part 42) about 8 mm from its tip to form an angle of about 70 degrees. Each of these bent guidewires was inserted inside a resin tube having an inner diameter of 0.5 mm, rotated inside the tube ten times, and thereafter pulled out of the tube. A rate of change in the angle in the bent portion was then measured. Moreover, after being further rotated ten times (rotated twenty times in total), the guidewire is pulled out of the tube, to measure a rate of change in angle in the bent portion. FIG. 7 illustrates averages of measured values obtained by conducting such a test several times.

It is to be noted that the inner diameter of the resin tube is set smaller than that of a blood vessel in which the guidewire 10 of the present embodiment is supposed to be used, for clarifying the difference upon comparison.

The comparative guidewire A does not have the inner coil 50, but uses the same core shaft 14 as that of the guidewire 10 of the present embodiment. Hence the diameter of the most distal portion 40 has been reduced. For this reason, in the test conducted by the ten-time rotation, there is not seen a large difference from the guidewire 10. However, in the test conducted by the twenty-time rotation, a rate of change in shaping angle is large. Namely, this indicates that in contrast with the guidewire 10 of the present embodiment, the angle formed by shaping of the comparative guidewire A remained widened inside the resin tube and was not restored, and the angle thereof changed. It is thus found that the inner coil 50 improves performance of retaining the shaping angle, as well as improving the foregoing rotation followability.

The comparative guidewire B does not have the inner coil 50. However, the comparative guidewire B was produced so as to have the stiffness in the range of about 5 to 20 mm of the tip being substantially the same value (namely, so as to have substantially the same stiffness curve) as the guidewire 10 of the present embodiment. Therefore, the core shaft of the comparative guidewire B is thicker than that of the guidewire 10 of the present embodiment. As a result, the rate of change in shaping angle is large in both cases of the ten-time rotation and the twenty-time rotation, as compared with the guidewire 10 of the present embodiment. Namely, it is found that the comparative guidewire B which makes almost the same change in stiffness as the guidewire 10 has sufficient stiffness for guiding the microcatheter, but the angle formed by shaping of the comparative guidewire B readily changes upon application of torque inside the blood vessel. It is therefore found that the guidewire 10 of the present embodiment ensures the stiffness for guiding the microcatheter, and also has performance improved for retaining the shaping angle.

FIG. 8 illustrates a result of comparing the restorability by use of the guidewire 10 of the present embodiment and the comparative guidewires A and B. In this test, each unshaped guidewire was inserted into a resin tube having a radius of 5.0 mm and an inner diameter of 0.5 mm, and curved to 180 degrees, and the guidewire was then pulled out. An amount of deformation of its tip portion, namely its most distal portion, was then measured. A rate of pulling at the time of pulling out the guidewire was set to about 600 mm/min. Further in this test, the guidewire was inserted into the tube such that the range about 55 mm from the tip of the guidewire where the guidewire is generally easy to bend, i.e., the range where the inner coil 50 is present in the guidewire 10, completely passes through the curved portion of the tube. Subsequently, the guidewire was pulled out, and an amount of deformation of the tip portion was measured. The amount of deformation of the tip portion was measured as a straight distance from the axial line of the core shaft extending substantially straight in the guidewire left in a natural state after being pulled out to the tip of the curved guidewire. FIG. 8 illustrates averages of the measured values obtained by performing such a test a plurality of times.

The comparative guidewire A uses the same core shaft 14 as that of the guidewire 10 of the present embodiment, though not having the inner coil 50. Therefore, as illustrated in FIG. 8, a large difference was not seen in amount of deformation of the tip portion (namely, a large difference was not seen in restorability) between the comparative guidewire A and the guidewire 10.

On the other hand, FIG. 8 indicates that the comparative guidewire B has a large amount of transformation of the tip portion and inferior restorability as compared with those of the guidewire 10. Namely, it is found that the comparative guidewire B making substantially the same change in stiffness as the guidewire 10 has sufficient stiffness for guiding the microcatheter, but upon receipt of external force inside the bent blood vessel, the comparative guidewire B is readily deformed and resistant to restoring.

It is therefore found that with the inner coil 50 provided, the guidewire 10 of the present embodiment ensures the stiffness for guiding the microcatheter, and also has the improved performance of retaining the shaped figure.

The following were found from the test results of FIGS. 7 and 8. Namely, in the guidewire 10 of the present embodiment, the tip portion, namely the most distal portion, of the core shaft 14 can be reduced in diameter by means of the inner coil 50. For this reason, this guidewire 10 maintains the stiffness for guiding the microcatheter, improves the performance of retaining the figure formed by shaping, and improves the restorability. Namely, an angle of a portion intentionally bent by shaping is maintained, and an unshaped portion can be prevented from being bent by external force during performance of the operation.

The action of the guidewire 10 of the present embodiment which has the foregoing configuration in the case of being used in an operation for a brain will be described based on FIG. 9.

The guidewire 10 is inserted from a femoral region or the like into an artery, passes through a cervical region, to reach an aneurysm 300 as a target region for treatment which is present in an artery 301 inside a brain. In this process, the guidewire 10 is used in combination with a microcatheter 200. At this time, the tip of the guidewire 10, in the state of being slightly projected from the tip of the microcatheter 200, is allowed to proceed just by a predetermined distance. Thereafter, to follow this tip, the microcatheter 200 is allowed to proceed. Upon reaching the vicinity of the tip of the guidewire 10 by the tip of the microcatheter 200, the guidewire 10 is again made to proceed by the predetermined distance. This is repeatedly performed, to make both of them come closer to a target position.

At this time, a predetermined portion on the tip side of the guidewire 10 comes into contact with a wall surface of a blood vessel. However, this predetermined portion coming into contact with the blood vessel wall is the flexible coil portion having the double coil structure made up of the inner coil 50 and the outer coil 60. Thereby, damage of the blood vessel can be prevented as much as possible.

Namely, the outer coil 60 and the inner coil 50 are joined to each other only by the coil joint 53. Therefore, the coils 50 and 60 are independent from each other with a space provided therebetween. Hence the flexibility of each of the coils 50 and 60 is not lost.

In particular, the inner coil 50 is a stranded coil made up of a plurality of strands 51. The guidewire 10 thus has a characteristic of being flexible, as well as a characteristic of high rotation followability. In the guidewire 10, the inner coil 50 is joined only to the outer coil 60 by the coil joint 53 except that both end portions of the inner coil 50 are joined to the core shaft 14. Namely, the intermediate portion of the inner coil 50 is not joined to the core shaft 14. With such a configuration, loss of the flexibility of the inner coil 50 can be prevented as much as possible. Therefore, the safety can be maintained, while the rotation followability as the characteristics of the stranded coil is enhanced.

As described above, the guidewire 10 prevents the change in stiffness of the core shaft 14 due to the inner coil 50. Further, the guidewire 10 has the structure to prevent, as much as possible, occurrence of the abrupt stiffness change, in view of the positional relation between the boundaries of the portions 62a, 62b and 63 and the inner rear end joint 52 and the coil joint 53 of the inner coil 50 because the stiffness of the portions 62a, 62b and 63 changes depending on the material constituting the outer coil 60 and depending on whether the coil is open coiled or close coiled are located. The guidewire 10 is thus provided with high rotation followability. Further, the pushability, which is the easiness to insert the guidewire 10 into the body in the axial direction, are also improved. Namely, the guidewire 10 does not have the portion where the stiffness abruptly changes. For this reason, when the guidewire 10 is operated on the proximal side and torque is applied to the guidewire 10, stagnation of transmission of the torque in the stiffness changing portion to cause deterioration in operability can be prevented as much as possible.

Figure 9:
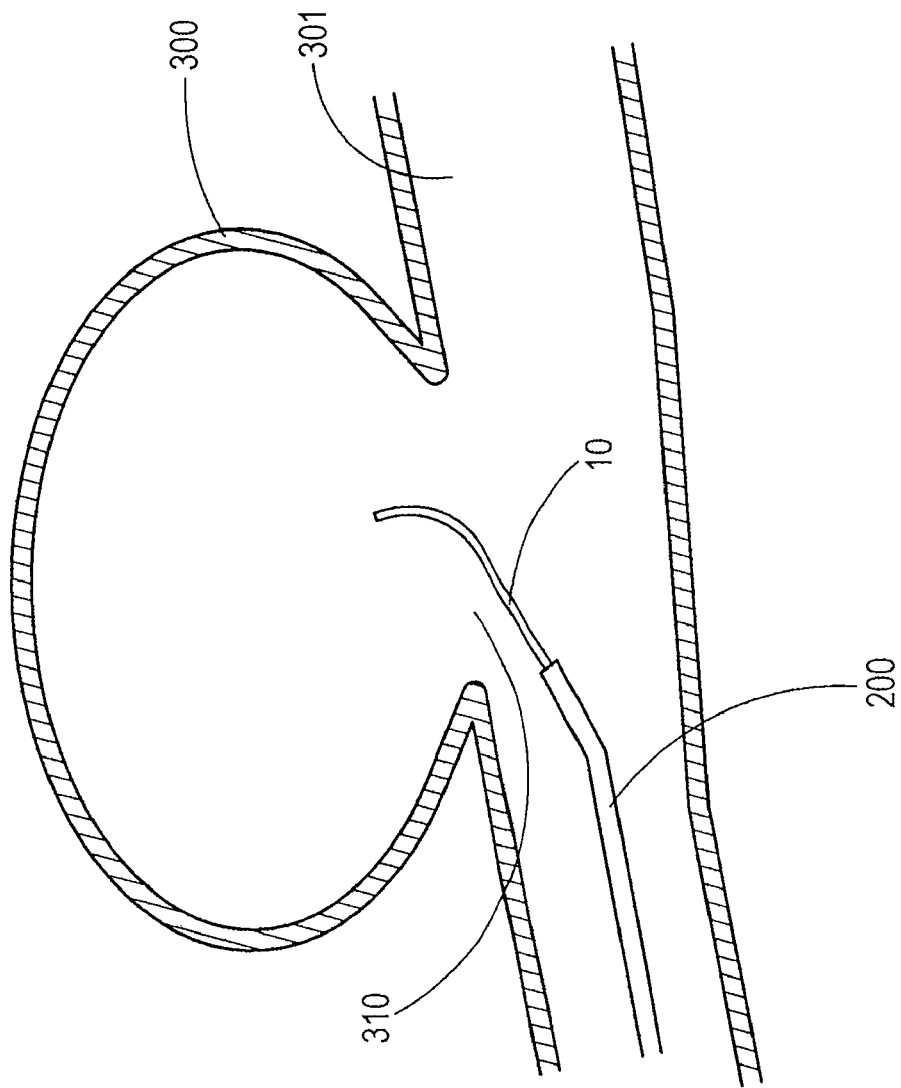
FIG. 9 illustrates an explanatory drawing of an operation of the guidewire of the present embodiment.

As schematically illustrated in FIG. 9, when the tip of the guidewire 10 is located in the vicinity of the aneurysm 300 inside the brain as the target region, an operation to insert the tip of the guidewire 10 toward the inside of the aneurysm 300 is performed so that the tip of the microcatheter 200 is allowed to enter the aneurysm 300. Generally, an angle is formed in the tip portion, usually the most distal portion 40, of the guidewire 10 by the conditioning, called shaping, to bend part of the tip portion of the guidewire 10 for forming an angle. This portion formed with the angle is rotated so as to be turned in the direction in which an opening 310 of the aneurysm 300 is present, and then enters the aneurysm 300. In this shaping, bending force is normally applied on the tip portion of the guidewire 10 from a direction orthogonal to the planes of the first flat part 43 and the second flat part 44. Thereby, this tip portion is bent to form an angle. The bent portion is different depending on the operation, but is generally in the range of the second flat part 44 to the fourth taper part 35 where the inner coil 50 is provided.

Especially the most distal portion 40 as a portion with a high probability of being shaped is located in the open coiled portion 62a of the outer coil 60. Therefore, spaces between the coils of the strand 61 in the open coiled portion 62a are also provided in the most distal portion 40 having the double coil structure made up of the outer coil 60 and the inner coil 50, thereby to facilitate execution of shaping.

The stiffness of the tip portion of the guidewire 10 is ensured by the inner coil 50. This allows the tip portion in the guidewire 10 to favorably guide the microcatheter 200 until the guidewire 10 reaches the vicinity of the aneurysm 300. Furthermore, even when the guidewire 10 passes through the inside of a narrow blood vessel till reaching the aneurysm 300, a change in angle formed by shaping which is provided at the tip of the guidewire 10 is prevented as much as possible, as obvious from the characteristics illustrated in FIG. 7. Moreover, as illustrated in FIG. 8, the restorability is improved in the guidewire 10. Accordingly, bending of the tip portion of the guidewire 10 can be prevented as much as possible even when the guidewire 10 passes through the inside of a tortuous, narrow blood vessel.

The tip of the guidewire 10 is directed toward the opening 310 of the aneurysm 300, after which the operation to insert the tip of the guidewire 10 inside the aneurysm 300 is performed with deliberation. As obvious from the characteristics illustrated in FIG. 5 described above, the guidewire 10 of the present embodiment indicates high rotation followability in the range near 0 to 90 degrees. Hence a delicate rotating manipulation on the proximal side of the guidewire 10 by the above operation is effectively transmitted to the distal side of the guidewire 10. It is thereby possible to facilitate this operation. Such effective transmission of the rotating manipulation is realized because the rotation torque from the outer coil 60 can be effectively transmitted to the inner coil 50 by joining the outer coil 60 and the inner coil 50 by the coil joint 53. Moreover, this effect is further enhanced by close-coiling the strands 61 of the outer coil 60 on the rear side of the coil joint 53.

In this operation, the tip portion of the guidewire 10 is rotated as described above, to turn the tip of the guidewire 10 in a desired direction. Thereafter, the microcatheter 200 is pushed ahead along the guidewire 10, to change the direction of the tip portion of the microcatheter 200. With the most distal portion 40 of the guidewire 10 provided with the first flat part 43 and the second flat part 44, the torsional stiffness is enhanced. This can facilitate the change in direction of the tip portion of the microcatheter 200. Further, the first flat part 43 for moderating the change in stiffness is provided on the rear end side of the second flat part 44. Accordingly, even when a large load acts on the tip portion of the guidewire 10 for changing the direction of the microcatheter 200, the most distal portion 40 of the core shaft 14 can be prevented as much as possible from being bent or kinked.

Moreover, the most distal portion 40 of the core shaft 14 is surrounded by the inner coil 50. This enables the inner coil 50 to receive a load that acts on the most distal portion 40 of the core shaft 14. It is therefore possible to further prevent the most distal portion 40 of the core shaft 14 from being bent or kinked.

By the foregoing operation, the microcatheter 200 reaches the target region along the guidewire 10. Thereafter, the guidewire 10 is extracted from the inside of the body, and a treatment with the microcatheter 200 is performed.

In the embodiment described above, the inner coil 50 is configured of the stranded coil made up of the plurality of strands 51. However, the inner coil 50 may also be a single wired coil made up of one strand although the rotation followability is not improved as much as in the case of the stranded coil. Even in the case of the single wired coil, the inner coil 50 is preferably a close coiled coil with adjacent coils of the strand being in substantially contact with each other from the viewpoint of the rotation followability.

The case of using the guidewire 10 for a brain has been described in the present embodiment. However, the guidewire 10 can be used for other organs than a brain, such as a heart.

Further, the number and size such as an outer diameter and an axial length of the taper part constituting the distal portion 30 and the most distal portion 40 and a cylindrical portion with a given outer diameter in the guidewire 10 can be changed as appropriate in accordance with desired stiffness.

Moreover, a variety of figures can be taken as the figure of the most distal portion 40. A variety of figures can be taken, such as a figure formed by combining a plurality of cylindrical shapes with a given outer diameter, and a shape with a plurality of plate-like flat parts each having a substantially rectangular cross section and a thickness that decreases toward the tip.

While the invention has been shown and described in detail, the foregoing description is in all aspects illustrative and not restrictive. It is therefore understood that numerous modifications and variations can be devised without departing from the spirit and scope of the invention.

REFERENCE SIGNS LIST 10 guidewire
14 core shaft
15 tip plug (tip joint)
30 distal portion
34 third taper part (intermediate taper part)
35 fourth taper part (front taper part)
40 most distal portion
41 large-diameter flexible part
42 small-diameter flexible part
43 first flat part
44 second flat part
50 inner coil
51 strand
52 inner rear end joint
53 coil joint
60 outer coil
61 strand
62 radiopaque portion
62a open coiled portion
62b close coiled portion
63 radiotransparent portion
64 outer rear end joint
65 outer intermediate joint

The invention claimed is:

1. A guidewire comprising:
a core shaft;
an inner coil that is formed by winding at least one strand, and surrounds a distal side portion of the core shaft;
an outer coil that is formed by winding at least one strand, and surrounds the inner coil and the distal side portion of the core shaft;
a tip joint that joins a distal end of the outer coil and a distal end of the inner coil to a distal end of the core shaft so as to form a gap between the core shaft and the inner coil and a gap between the inner coil and the outer coil;
an outer proximal end joint that joins a proximal end of the outer coil to the core shaft;
an inner proximal end joint that joins a proximal end of the inner coil to the core shaft so as to form a gap between the inner coil and the outer coil on a distal side of the outer proximal end joint; and
a coil joint that is located between the tip joint and the inner proximal end joint, and joins only the outer coil and the inner coil to each other so as to form a gap between the inner coil and the core shaft.

2. The guidewire according to claim 1, wherein the inner coil is a hollow stranded coil formed by stranding a plurality of strands.

3. A guidewire comprising:
a core shaft having a distal end;
an inner coil that is formed by winding at least one strand, and surrounds a distal side portion of the core shaft;
an outer coil that is formed by winding at least one strand, and surrounds the inner coil and the distal side portion of the core shaft;
a tip joint that joins a distal end of the outer coil and a distal end of the inner coil to the distal end of the core shaft so as to form a first gap between the core shaft and the inner coil and a second gap between the inner coil and the outer coil;
an outer proximal end joint that joins a proximal end of the outer coil to the core shaft;
an inner proximal end joint that joins a proximal end of the inner coil to the core shaft so as to form a third gap between the inner coil and the outer coil on a distal side of the outer proximal end joint; and
a coil joint that is located between the tip joint and the inner proximal end joint, and joins only the outer coil and the inner coil to each other so as to form a fourth gap between the inner coil and the core shaft.

4. The guidewire according to claim 3, wherein the inner coil is a hollow stranded coil formed by stranding a plurality of strands.

* * * * *